United States Patent
Nicolas et al.

(10) Patent No.: US 10,408,795 B2
(45) Date of Patent: Sep. 10, 2019

(54) METHOD OF CHECKING A FLEXIBLE LINE AND ASSOCIATED INSTALLATION

(71) Applicant: TECHNIP FRANCE, Courbevoie (FR)

(72) Inventors: Yann Nicolas, Rueil-Malmaison (FR); Philippe Lembeye, Montigny (FR)

(73) Assignee: TECHNIP FRANCE (FR)

( * ) Notice: Subject to any disclaimer, the term of this patent is extended or adjusted under 35 U.S.C. 154(b) by 47 days.

(21) Appl. No.: 15/540,707

(22) PCT Filed: Dec. 30, 2015

(86) PCT No.: PCT/EP2015/081429
§ 371 (c)(1),
(2) Date: Jun. 29, 2017

(87) PCT Pub. No.: WO2016/107909
PCT Pub. Date: Jul. 7, 2016

(65) Prior Publication Data
US 2017/0350866 A1  Dec. 7, 2017

(30) Foreign Application Priority Data
Dec. 30, 2014 (FR) ..................... 14 63446

(51) Int. Cl.
*G01N 29/032* (2006.01)
*G01N 29/11* (2006.01)
(Continued)

(52) U.S. Cl.
CPC ........... *G01N 29/04* (2013.01); *G01N 29/032* (2013.01); *G01N 29/11* (2013.01);
(Continued)

(58) Field of Classification Search
CPC ............... G01N 29/04; G01N 29/2437; G01N 29/4427; G01N 29/032; G01N 29/11; G01N 2291/0422
(Continued)

(56) References Cited

U.S. PATENT DOCUMENTS 6,427,524 B1 * 8/2002 Raspante ............ G01M 3/3218
73/45.4
8,048,386 B2 * 11/2011 Dority ..................... B01L 3/502
422/500
(Continued)

FOREIGN PATENT DOCUMENTS

| FR | 2 835 317 A1 | 8/2003 |
| GB | 2 446 670 A | 8/2008 |
| GB | 2 495 406 A | 4/2013 |

OTHER PUBLICATIONS

International Search Report dated Mar. 16, 2016 in corresponding PCT International Application No. PCT/EP2015/081429.
(Continued)

*Primary Examiner* — Jacques M Saint Surin
(74) *Attorney, Agent, or Firm* — Ostrolenk Faber LLP

(57) ABSTRACT

A method for checking a flexible line, the flexible line including at least one layer of armors (24, 25) surrounded by an external sheath (30), the external sheath (30) delimiting an internal space (33) receiving the layer of armors (24, 25) and including at least one medium (M) at the interface between the external sheath (30) and the internal space (33). The method includes sending an ultrasonic signal on a region to be checked of the external sheath (30), and receiving the reflected signal at the interface between the region to be checked of the external sheath (30) and the internal space (33) facing the region to be checked of the external sheath (30); and analyzing the polarity of the reflected signal and determining, according to the analyzed
(Continued)

polarity, at least the nature of the medium (M) at the interface.

18 Claims, 2 Drawing Sheets

(51) Int. Cl.
G01N 29/44 (2006.01)
G01N 29/24 (2006.01)
G01N 29/04 (2006.01)

(52) U.S. Cl.
CPC ..... *G01N 29/2437* (2013.01); *G01N 29/4427* (2013.01); *G01N 2291/0422* (2013.01)

(58) Field of Classification Search
USPC .......................................................... 73/632
See application file for complete search history.

(56) References Cited

U.S. PATENT DOCUMENTS

| | | | |
|---|---|---|---|
| 9,658,421 B2* | 5/2017 | Do | F16L 11/083 |
| 2013/0104664 A1* | 5/2013 | Chevalier, Jr. | G01M 3/36 |
| | | | 73/763 |
| 2013/0125655 A1 | 5/2013 | Klopffer et al. | 73/592 |
| 2014/0165709 A1* | 6/2014 | Clements | G01N 3/12 |
| | | | 73/49.5 |

OTHER PUBLICATIONS

Written Opinion dated Mar. 16, 2016 in corresponding PCT International Application No. PCT/EP2015/081429.
French Preliminary Search Report dated Nov. 30, 2015 in corresponding French Patent Application No. 1463446.

* cited by examiner

METHOD OF CHECKING A FLEXIBLE LINE AND ASSOCIATED INSTALLATION

CROSS-REFERENCE TO RELATED APPLICATIONS

The present application is a 35 U.S.C. §§ 371 national phase conversion of PCT/EP2015/081429, filed Dec. 30, 2015, which claims priority to French Patent Application No. 1463446, filed Dec. 30, 2014, the contents of which are incorporated herein by reference. The PCT International Application was published in the French language.

BACKGROUND AND SUMMARY OF THE INVENTION

The present invention relates to a method for controlling a flexible line comprising at least a layer of armors surrounded by an external sheath, the external sheath delimiting an inner space receiving the layer of armors and comprising at least one medium at the interface between the external sheath and the internal space, the method comprising:
  the sending of an ultrasonic signal from the outside of the external sheath onto a region to be controlled of the external sheath, and
  the reception of the signal reflected at the interface between the region to be controlled of the external sheath and the inner space facing the region to be controlled of the external sheath.

The invention also relates to an installation for controlling a flexible line.

In particular, the method is intended for detecting flooding of the space present inside the external sheath, notably flooding of the layers of traction armors present in the flexible line.

The flexible line is advantageously a flexible conduit of the unbonded type intended for the transport of hydrocarbons through an extent of water, such as an ocean, a sea, a lake or a river. Alternatively, the flexible line is a reinforced umbilical line with elements of armor or further a cable.

Such a flexible conduit is for example made according to the normative documents API 17J (Specification for Unbonded Flexible Pipe) and API RP 17B (Recommended Practice for Flexible Pipe) established by the American Petroleum Institute.

The conduit is generally formed with a set of concentric and superposed layers. It is considered as "unbonded" in the sense of the present invention from the moment that at least one of the layers of the conduit is able to be moved longitudinally relatively to the adjacent layers during flexure of the conduit. In particular, an unbonded conduit is a conduit without any binding materials connecting layers forming the conduit.

The conduit is generally positioned through an extent of water, between a bottom assembly, intended to collect the fluid exploited in the bottom of the extent of water and a fixed or floating surface assembly, intended to collect and distribute the fluid. The surface assembly may be a semi-submersible platform, an FPSO or another floating assembly.

The conduits intended for great depths also have to resist to very strong tensions, currently several tens of tons, to which they are subject during operation and/or during their installation in the sea.

Further, in the case when the surface assembly is floating and mobile depending on the sea conditions, the riser conduits ("risers") connecting the sea bottom to the surface assembly may sometimes be subject to millions of curvature variation cycles. These riser conduits therefore should also be capable of resisting durably to dynamic fatigue stresses.

In order to guarantee such a strength in tension during the whole lifetime of the conduit, it is necessary to ensure the integrity of the layers of traction armors, generally made from helical windings of metal wires. In particular, the layers of armors are in certain cases sensitive to corrosion. The corrosion may be induced by the permeation of acid compounds present in the transported fluid and/or by the presence of water in the space receiving the layers of armors.

The presence of water may notably appear during a flaw or breakage of the external sheath which then no longer ensures its protective function of the conduit.

In order to detect possible flaws or breakages of the external sheath leading to flooding of the internal space, different tests are applied, such as the annular test. The annular test consists of measuring the current volume of gas of the annular portion of the flexible conduit for example by applying vacuum in the annular portion. The measured current volume of gas is compared with the initial volume of the annular portion so as to infer therefrom whether water has invaded partly or totally the annular portion. However, such a volume measurement is often not very accurate and therefore does not give the possibility of determining the presence and the height of possible flooded areas threatening the integrity of the flexible conduit.

GB-B-2 446 670 describes an underwater inspection method for the integrity of the annular portion of a flexible conduit based on the ultrasonic echography technique. According to this method, an ultrasonic probe emits an ultrasonic wave which penetrates into the conduit. In return, the probe receives the ultrasonic waves reflected at the discontinuities, i.e. at the interfaces, encountered in the conduit. The amplitudes of the reflected waves notably give the possibility of determining whether the portion of the inspected conduit is flooded.

Such a method is based on a property of ultrasonic waves according to which the ultrasonic waves do not propagate very much in a gas as opposed to a liquid medium such as water.

However, such a property is not verified in a medium subject to external pressure. Indeed from a certain pressure level between two materials, the ultrasonic waves propagate in the absence of a coupling medium such as a liquid. For example, from a few tens of bars of contact pressure, ultrasonic waves propagate between a thermoplastic sheath and a metal layer without any coupling medium.

The coupling pressure between the external sheath and the elements of armors mainly depend on the internal pressure of the flexible conduit and on the hydrostatic pressure. The coupling pressure therefore varies according to the depth at which the measurement is conducted.

Thus, when the contact pressure between the external sheath and the elements of armors is greater than a few tens of bars, the inspection method shown in patent GB-B-2 446 670 does not give the possibility of making a distinction between a flooded annular portion and a dry annular portion.

The object of the invention is to provide a method for controlling the integrity of a flexible conduit, in particular of the annular portion of the flexible conduit, which is not intrusive, simple to apply and reliable regardless of the outer pressure applied to the flexible conduit.

For this purpose, the object of the invention is a method of the aforementioned type, further comprising the analysis of the polarity of the signal reflected at the interface and the determination, according to the analyzed polarity, of at least the nature of the medium at the interface.

The method according to the invention may comprise one or several of the following characteristics, taken individually or according to any technically possible combination:

- during the analysis step, the reflected signal is not rectified.
- the method further includes the sweeping of a plurality of regions to be controlled successively of the external sheath and the repetition, for each region to be controlled of the external sheath, of steps for sending, receiving, analyzing and determining the medium at the interface between the region to be controlled of the external sheath and the internal space facing the region to be controlled of the external sheath.
- the sweeping pitch is comprised between 0 millimeter and 10 millimeters and advantageously between 0 mm and 2 mm.
- the sweeping is carried out axially along the flexible line and/or angularly around the flexible line.
- the sweeping is carried out by using a probe sending the ultrasonic signal borne by a mobile displacement support of the probe.
- the mobile support is a motor-driven manipulator attached around the flexible line by means of a underwater robot of the conduit, a mobile manipulator capable of moving along the conduit and/or a mobile support able to be grasped by the hand of a diver.
- the sent ultrasonic signal has a central frequency selected from between 1.5 MHz and 5 MHz, preferentially between 2 MHz and 2.5 MHz.
- the ultrasonic signal is sent in the form of a focussed ultrasonic beam.
- the ultrasonic signal is sent and received by a piezoelectric sensor.
- during the determination step, the reflected signal is compared with a database of ultrasonic signals.
- the flexible line includes an intermediate layer between the external sheath and the layer of armors.
- the medium is a liquid, a gas or a solid.
- the method is applied during the use of the flexible line, in particular during the passage of a fluid through a central passage of the flexible line.
- the external sheath is immersed in an extent of water, the sending of the ultrasonic signal being carried out by means of a probe oriented towards the external surface of the external sheath.

The object of the invention is also an installation for controlling a flexible line comprising at least one layer of armors surrounded with an external sheath, the external sheath delimiting an internal space receiving the layer of armors and comprising at least one medium at the interface between the external sheath and the internal space, the installation comprising:

- a probe able to send an ultrasonic signal on a region to be controlled of the external sheath and of receiving the reflected signal at the interface between the region to be controlled of the external sheath and the internal space facing the region to be controlled of the external sheath, and
- a data processing unit configured for analyzing the polarity of the signal reflected at the interface and determining, according to the analyzed polarity, at least the nature of the medium at the interface.

BRIEF DESCRIPTION OF THE DRAWINGS

The invention will be better understood upon reading the description which follows only given as an example, and made with reference to the appended drawings, wherein.

DESCRIPTION OF PREFERRED EMBODIMENTS

In all the following, the terms of "outer" and "inner" are generally meant radially relatively to an axis X-X' of the conduit, the term of "outer" being understood as relatively radially farther than the X-X' axis and the term of "inner" being understood as relatively radially closer to the axis X-X' of the conduit.

The terms of "front" and "rear" are meant axially relatively to an axis X-X' of the conduit, the term of "front" meaning relatively farther from the medium of the conduit and closer to one of its ends, the term "rear" meaning relatively closer to the medium of the conduit and farther from one of its ends. The medium of the conduit is the point of the conduit located at an equal distance from both ends of the latter.

Figure 1:
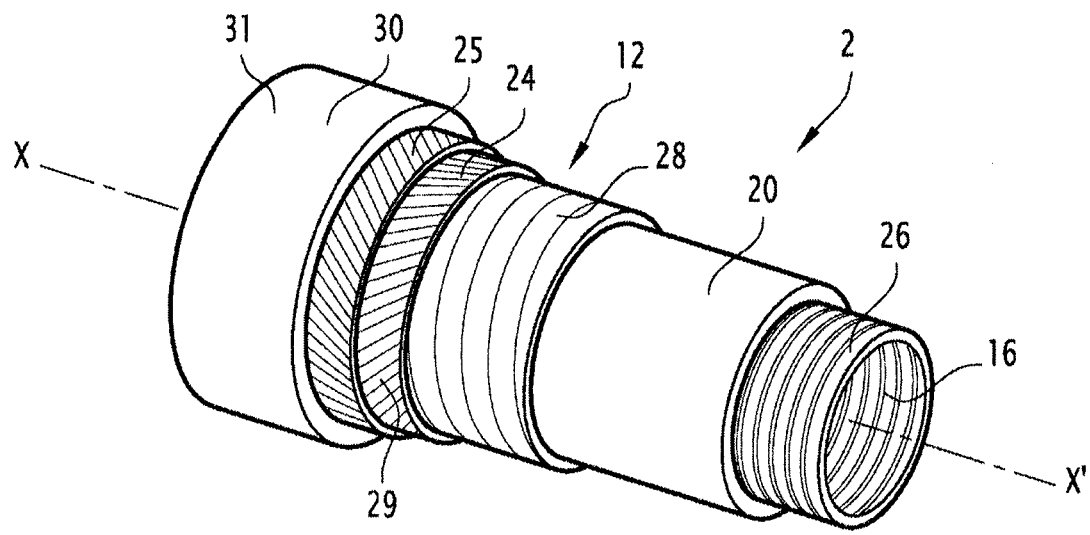
FIG. 1 is a partly cutout perspective view of a central segment of a first flexible conduit controlled by means of a method according to the invention, the flexible conduit comprising an external sheath.
Figure 2:
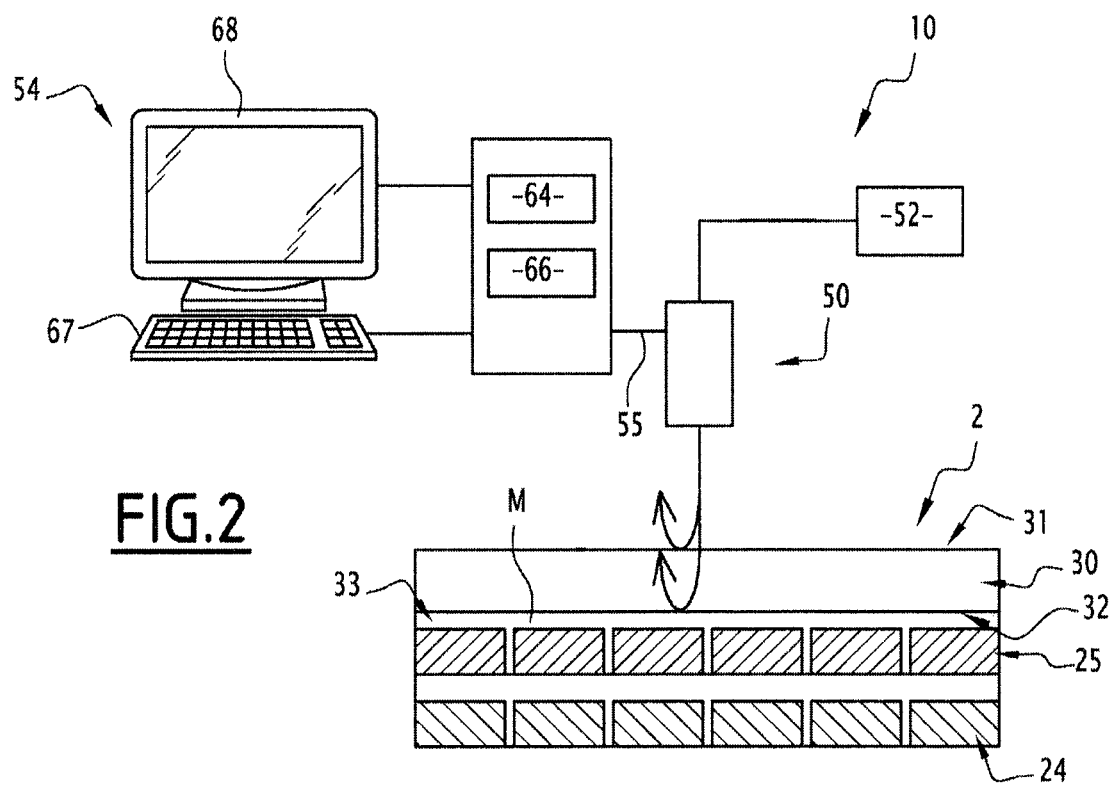
FIG. 2 is a partial sectional view along a middle axial plane, of relevant layers of the flexible conduit and a control installation according to the invention.

FIG. 1 partly illustrates a flexible line 2. FIG. 2 illustrates an installation 10 according to the invention for controlling the flexible line 2 of FIG. 1.

In the example described hereafter, the flexible line 2 is a flexible conduit. Alternatively, the flexible line 2 is a cable or an umbilical line.

The flexible conduit 2 includes a central segment 12 partly illustrated in FIG. 1. The conduit 2 delimits a central passage 16 for circulation of a fluid, advantageously a petroleum fluid. The central passage 16 extends along an axis X-X', between the upstream end and the downstream end of the conduit 2.

The flexible conduit 2 is intended to be positioned through an extent of water (not shown) in an installation for exploiting fluid, notably hydrocarbons. The extent of water is for example a sea, a lake or an ocean. The depth of the extent of water at right angles to the installation for exploiting fluids is for example comprised between 100 meters (m) and 3,000 meters.

The installation for exploiting fluid includes a surface assembly notably a floating assembly and a bottom assembly (not shown) which are generally connected between them with the flexible conduit 2.

The flexible conduit 2 is preferably an "unbonded" conduit.

At least two adjacent layers of the flexible conduit 2 are free to move longitudinally relatively to each other during flexure of the conduit 2.

Advantageously, all the layers of the flexible conduit 2 are free to move relatively to each other. Such a conduit 2 is for example described in the normative documents published by the American Petroleum Institute (API), API 17J, and API RP17B.

As illustrated by FIG. 1, the conduit 2 delimits a plurality of concentric layers around the axis X-X', which continuously extend along the central segment 12.

The conduit 2 includes, for example, at least one first tubular sheath 20 based on a polymeric material advantageously making up a pressure sheath.

The conduit 2 includes, additionally, at least one layer of traction armors 24, 25 positioned on the outside relatively to the first sheath 20 forming a pressure sheath.

In this example, the conduit 2 further includes an internal carcass 26 positioned inside the pressure sheath 20, a pressure vault 28 inserted between the pressure sheath 20 and the traction armor layer(s) 24, 25 and an external sheath 30, intended for protecting the conduit 2.

In a known way, the pressure sheath 20 is intended to sealably confine the transported fluid in the passage 16. It is formed in a polymeric material, for example based on a polyolefin such as polyethylene, based on a polyamide such as PA11 or PA12, or based on a fluorinated polymer such as polyvinylidene fluoride (PVDF).

The thickness of the pressure sheath 20 is for example comprised between 5 mm and 20 mm.

The carcass 26 is for example formed with a profiled metal sheet, spirally wound. The turns of the sheet are advantageously stapled with each other. The main function of the carcass 26 is to absorb the radial crushing forces.

The carcass 26 is for example totally metal.

In this example, the carcass 26 is positioned inside the pressure sheath 20. The conduit 2 is then designated by the term of «rough bore» because of the geometry of the carcass 26.

The carcass 26 is able to come into contact with the fluid circulating in the pressure sheath 20.

The helicoidal winding of the profiled metal sheet forming the carcass 26 is with a short pitch, i.e. it has a helix angle with an absolute value close to 90°, typically comprised between 75° and 90°.

Alternatively, the flexible conduit 2 is without any internal carcass 26. The flexible conduit 2 is then designated by the term of «smooth bore».

In this example, the pressure vault 28 is intended to absorb the forces related to the pressure prevailing inside the pressure sheath 20. It is for example formed with a metal profiled wire wound as a helix around the sheath 20. The profiled wire generally has a complex geometry, notably Z, T, U, K, X or I-shaped.

The pressure vault 28 is wound as a helix with a short pitch around the pressure sheath 20, i.e. with a helix angle with an absolute value close to 90°, typically comprised between 75° and 90°.

The flexible conduit 2 according to the invention at least comprises a layer of armors 24, 25 formed with a helical winding of at least one elongated armor element 29.

In the example illustrated in FIG. 1, the flexible conduit 2 includes two layers of armors 24, 25, notably an inner layer of armors i24, applied on the pressure vault 28 and an outer layer of armors 25 around which is positioned the outer sheath 30.

Each layer of armors 24, 25 includes longitudinal armor elements 29 wound with a long pitch around the axis X-X' of the conduit 2.

By «wound with a long pitch», is meant that the absolute value of the helix angle is less than 60°, and is typically comprised between 25° and 55°.

The armor elements 29 of a first layer 24 are generally wound according to an angle opposed relatively to the armor elements 29 of a second layer 25. Thus, if the winding angle of the armor elements 29 of the first layer 24 is equal to $+\alpha$, $\alpha$ being comprised between 25° and 55°, the winding angle of the armor elements 29 of the second layer of armors 25 positioned in contact with the first layer of armors 24 is for example equal to $-\alpha°$.

The armor elements 29 are for example formed with metal wires, notably steel wires, or with ribbons in composite material, for example ribbons reinforced with carbon fibers.

The external sheath 30 is intended to prevent the permeation of fluid from the outside of the flexible conduit 2 towards the inside. It is advantageously made in a polymeric material, notably based on a polyolefin, such as polyethylene, or based on a polyamide, such as PA11 or PA12.

As visible in FIG. 2, the external sheath 30 comprises an external surface 31 oriented towards the outside of the flexible conduit 2 and an internal surface 32 oriented towards the inside of the flexible conduit 2 and therefore to the second layer of armors 25.

The thickness of the external sheath 30 is for example comprised between 5 mm and 15 mm.

As visible in FIG. 2, the internal space located between the external sheath 30 and the pressure sheath 20 is called an annular space 33. The annular space 33 comprises at least one medium M. One of the object of the present invention is to control the integrity of the annular space 33 of the flexible conduit 2 notably by determining the medium(a) M present in the annular space 33 notably at the interstice between the external sheath 30 and the layers of armors 24, 25. The media M are for example selected from a liquid such as water, a gas such as air and a solid in the absence of any interstice. For example, when one of the media M present in the annular space 33 is water, the annular space 33 is considered as being flooded.

As illustrated in FIG. 2, the installation 10 for control according to the invention comprises a probe 50, a movable support 52 for displacement of the probe 50 and a computer 54.

The probe 50 is an ultrasonic probe configured for sending and receiving ultrasonic waves.

The probe 50 is connected to the computer 54, for example via a connection cable 55.

The probe 50 notably comprises an ultrasonic transducer.

The ultrasonic transducer is able to generate an ultrasonic signal with a central frequency comprised between 1.5 Megahertz (MHz) and 5 MHz, preferentially between 2 MHz and 2.5 MHz.

The ultrasonic transducer is advantageously focused. The focusing may be obtained with ultrasonic lenses, by mirrors with suitable shapes, for shaping the piezo-electric transducer, notably if this is an ultrasonic transducer of the piezocomposite type, or by a mosaic of elementary transducers electronically phased-shifted ("phased array").

The ultrasonic transducer is for example a piezo-electric sensor.

The movable support 52 is configured for transporting and displacing the probe 50 on the flexible conduit 2 so that the probe 50 sweeps several successive regions of the flexible conduit 2.

The movable support 52 is for example a motor-driven fixed manipulator around the flexible conduit 2 by means of an underwater robot, notably a remote-controlled vehicle ("Remotely Operated Vehicle" or "ROV"). This underwater robot is used for setting, moving and removing the manipulator, as well as for transmitting the signals towards the surface. Alternatively, the motor-driven manipulator is able to move along the conduit 2 with its own means.

According to another embodiment, the movable support 52 is able to be grasped by the hand of a diver in order to be displaced.

The mobile support 52 is able to displace the probe 50 longitudinally along the conduit 2 for carrying out successive measurements of regions to be checked of the flexible conduit 2. Advantageously, the movable support 52 is able to displace the probe 50 around the axis X-X' of the conduit 2 in order to conduct angular measurements of the nature of the medium M in the regions to be checked.

The sweeping pitch of the movable support 52 is for example comprised between 0 millimeter (mm) and 100 mm, advantageously between 0 mm and 10 mm, preferentially between 0 mm and 2 mm.

The computer 54 is able to represent the reflected signals measured by the ultrasonic transducer in a A-scan, B-scan or further C-scan view.

An A-scan view is a representation of the amplitude of the reflected signals versus time. An A-scan view corresponds to a fixed position of the transducer relatively to the checked part, and represents the different ultrasonic echoes versus time.

A B-scan view provides a representation as an image of a cross-section of the checked part. A B-scan view is obtained either by displacing a single element ultrasonic transducer along a line parallel to the surface of the checked part (mechanical sweeping of the checked part), or by using a multi-element ultrasonic transducer wherein the elements are aligned as a linear bar and may be sequentially queried via a multiplexing device (electronic sweeping of the checked part). The first dimension of this image corresponds to the travel time of the ultrasonic wave. The second dimension of this image corresponds to the amplitude of the mechanical or electronic displacement of the ultrasonic beam parallel to the surface of the part. Each pixel is color-coded or with a gray scale depending on the amplitude of the reflected signal at the corresponding point. A B-scan view is in fact a juxtaposition of A-scan views wherein the amplitudes of the reflected signals are color-coded or in gray levels.

A C-scan view provides a representation as an image of a top view of the inspected part. A C-scan view is obtained either by displacing a single element transducer along two axes perpendicular to each other and parallel to the surface of the part to be checked (dual mechanical sweep), or by displacing a multi-element linear transducer (combination of a mechanical sweep and of an electronic sweep), or by using an immobile multi-element matrix sensor (dual electronic sweep). Both dimensions of this image correspond to the amplitudes of the mechanical and/or electronic displacements of the ultrasonic beam along two axes perpendicular to each other, and parallel to the surface of the checked part. Each pixel of this image therefore corresponds to a particular position of the ultrasonic beam relatively to the checked part. The reflected signal corresponding to this pixel is therefore treated so as to be coded in color or in a gray level. A conventional treatment consists of searching for the largest reflected echo in the checked part, of measuring the amplitude of this largest echo, of coding this amplitude in color or in a gray level and of representing the corresponding pixel according to this coding. Other treatments are possible, for example a treatment consisting of coding the color or the gray level of each pixel according to the travel time corresponding to the echo of the largest amplitude reflected by the part.

The computer 54 is for example a computer including a data processing unit 64 and a memory 66, as well as optionally a keyboard 67 and a display unit 68.

The computer 54 is advantageously loaded onboard the underwater robot connected to the motor-driven manipulator so as to limit the cable length between the probe 50 and the computer 54, in order not to degrade the transmission of high frequency analogue signals sent by the probe 50. The computer 54 is able to process in real time these analogue signals and to send back the result of this processing as digital signals. These digital signals may be transmitted over a great distance as far as the surface installation, i.e. at the surface of the water extent in which is generally immersed the flexible conduit 2, via the underwater robot and via an umbilical cable connecting the underwater robot to the surface.

The data processing unit 64 is configured for analyzing the polarity of the reflected signals at the interface between the external sheath 30 and the annular space 33 facing regions to be checked of the external sheath 30.

The data processing unit 64 is further configured for determining, according to the analyzed polarity, at least the nature of the media M present in the annular space 33 facing regions to be checked of the external sheath 30. The nature of a medium M is for example water, air or a metal.

A database of ultrasonic signals is also stored in the memory 66 of the processor 58. The database notably comprises characteristics of the reflected ultrasonic signals at different interfaces, for example between the external sheath 30 and air, between the external sheath 30 and water and between the external sheath 30 and a metal. The characteristics are notably reflection coefficients at the interfaces and the polarities of the reflected signals relatively to the incident signals.

The reflection coefficient is defined as the amplitude of a reflected wave over the amplitude of the associated incident wave, or the intensity of the reflected wave over the intensity of the associated incident wave. The polarity of the reflected signal relatively to the incident signal is the sign of the reflected signal as compared with the sign of the incident signal.

Figure 3:
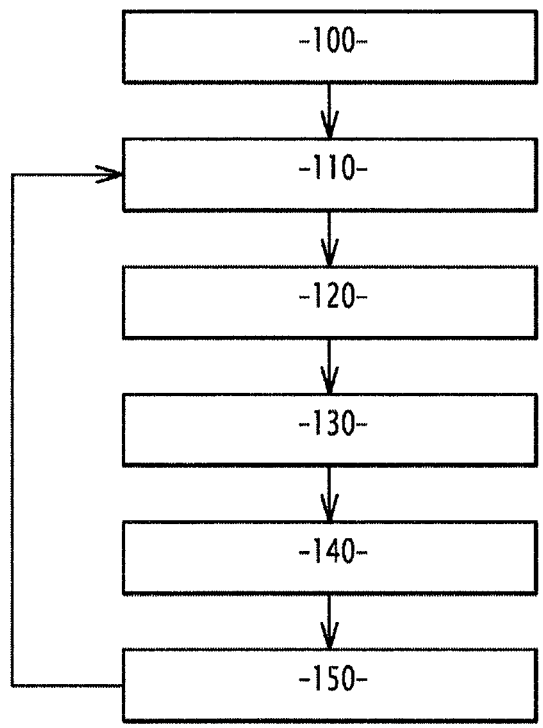
FIG. 3 is a flow chart of an example of application of a control method according to the invention.

The operation of the checking installation 10 will now be described with reference to FIG. 3, which is a flow chart of an exemplary application of a checking method according to the invention.

The control method comprises a first step 100 for positioning the probe 50 facing a region to be checked of the flexible conduit 2. The probe 50 is oriented towards the external surface 31 of the external sheath 30.

The positioning step 100 is applied by the movable support 52.

The method then comprises at each stop of the movable support 52 and therefore of the probe 50, a step 110 for sending an ultrasonic signal onto the external surface 31 of the external sheath 30. The ultrasonic signal is sent on a region to be checked of the external sheath 30 from the outside of the external sheath 30.

As the ultrasonic signal is focussed on the external sheath 30, a region of the external sheath 30 is notably delimited by the focussing spot formed by the incident ultrasonic beam on the external sheath 30.

The central frequency of the ultrasonic waves is comprised between 1.5 MHz and 5 MHz, preferentially between 2 MHz and 2.5 MHz.

The sending step 110 is applied by the probe 50.

The method then comprises a step 120 for receiving reflected ultrasonic signals at the different interfaces encountered by the signal. An interface is defined as a surface between two media. Thus, the first interface encountered by the incident ultrasonic signal is the interface between water and the external sheath 30 when the flexible conduit 2 is positioned in an extent of water. The second interface is the interface between the external sheath 30 and the annular space 33 facing the region to be checked of the external sheath 30. The third optional interface is the interface between the annular space 33 facing the region to be checked of the external sheath 30 and the second layer of armors 25 facing the region to be checked of the external sheath 30.

Figure 4:
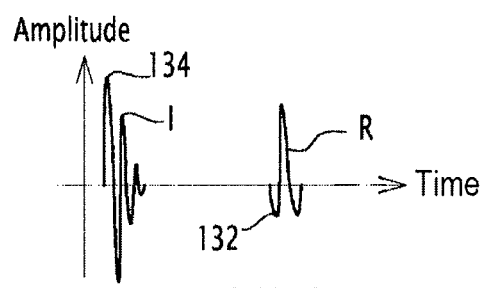
FIG. 4 is a graph representing an incident ultrasonic signal and a reflected ultrasonic signal at the interface between the external sheath of FIG. 1 and air.
Figure 5:
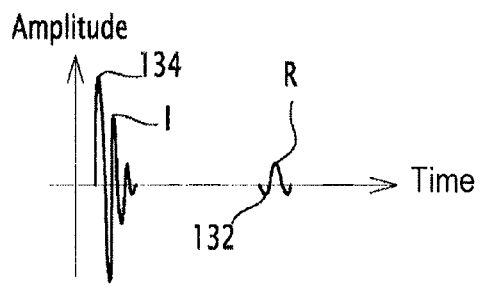
FIG. 5 is a graph representing an incident ultrasonic signal and a reflected ultrasonic signal at the interface between the external sheath of FIG. 1 and water.
Figure 6:
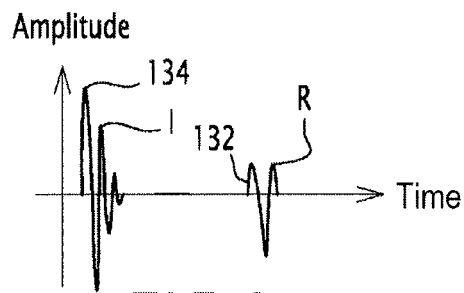
FIG. 6 is a graph representing an incident ultrasonic signal and a reflected ultrasonic signal at the interface between the external sheath of FIG. 1 and a steel material.

In FIGS. 4 to 6, are illustrated different signals reflected at the interfaces between the internal surface 32 of the external sheath 30 and the annular space 33 located facing the region to be checked of the external sheath 30 when the annular space 33 comprises different media M.

The received signals are then transmitted to the computer 54 via the connection cable 55.

The receiving step 120 is applied by the probe 50.

The method then comprises a step 130 for analyzing the reflected signals.

The analysis step 130 comprises a first phase for determining the signal at the interface between the internal surface 32 of the external sheath 30 and the medium M of the annular space facing the region to be checked of the external sheath 30, from among the whole of the reflected signals. The first phase consists of comparing the flight times associated with the different reflected signals. The flight time of a reflected signal is actually the duration separating the emission of an incident signal from the reception of the reflected signal. The reflected signals are then classified by the order of arrival, which gives the possibility of inferring therefrom the reflected signal at the second interface, i.e. at the interface between the internal surface 32 of the external sheath 30 and the annular space 33 facing the region to be checked of the external sheath 30.

The analysis step 130 then comprises a phase for determining the amplitude of the reflected signal at the second interface and for calculating the ratio of the amplitudes between the reflected signal and the incident signal. The ratio of the amplitudes calculated is the reflection coefficient of the ultrasonic wave for the second interface.

The analysis step 130 then comprises, a phase for determining the polarity of the reflected signal R at the second interface relatively to the polarity of the incident signal I. With reference to FIG. 4 or to FIG. 5, when the first peak 132 of the reflected signal R is of a sign opposite to the sign of the first peak 134 of the incident signal I, the polarity of the reflected signal R is said to be inverted relatively to the polarity of the incident signal I. With reference to FIG. 6, when the first peak 132 of the reflected signal R is of the same sign as the first peak 134 of the incident signal I, the polarity of the reflected signal R is said to be identical with the polarity of the incident signal I.

Thus, the second interface is defined by the determined reflection coefficient and by the polarity of the reflected signal R relatively to the incident signal I.

During the analysis step 130, the analyzed reflected signal is not rectified, i.e. the electric signal sent back by the probe 50 is simply amplified before the analysis step, this amplification being insured without any modification of the shape of the signal.

The analysis step 130 is applied by the processing unit 64 of the computer 54.

The checking method then comprises, a step for determining 140 the medium M delimiting the second interface.

During this determination step 140, the reflected signal is compared with the database of ultrasonic signals. In particular, the calculated reflection coefficient during the analysis step 130 is compared with the reflection coefficients referenced in the database and the polarity determined during the analysis step 130 is compared with the polarities of the database.

For example, the database groups the pieces of information of the following table:

| Interfaces | Polarity | Reflection coefficient | Figures of the request |
| --- | --- | --- | --- |
| External sheath and air | Reversed polarity | ≥99% | FIG. 4 |
| External sheath and water | Reversed polarity | ≤1% | FIG. 5 |
| External sheath and steel | Identical polarity | comprised between 80% and 90% | FIG. 6 |

The pieces of information contained in the database stem from experimental measurements or from theoretical calculations.

When an interface of the database between the external sheath 30 and a medium M has a reflection coefficient substantially equal to the reflection coefficient determined during step 130 and a polarity identical with the polarity determined during step 130, the medium M of the second interface is considered as identical with the medium of the interface of the database. Thus, the medium M is determined. If the medium M is water, the annular space 33 of the flexible conduit 2 is considered as flooded at the checked region of the external sheath 30. By the expression of «substantially equal» is meant equal with an uncertainty of 5%.

The determination step 140 is applied by the processing unit 64 of the computer 54.

The checking method then comprises a step for displacement 150 of the probe 50 on the flexible conduit 2 depending on the sweep pitch of the movable support 52. Such a displacement step 150 thus gives the possibility to the probe 50 of having access to different regions of the flexible conduit 2. The sweep is carried out axially along the flexible conduit 2 along the axis X-X' and/or angularly around the flexible conduit 2, i.e. the probe 50 rotates around the flexible conduit 2.

The displacement step 150 is applied by the movable support 52.

Next, the checking method comprises, for each region of the flexible conduit 2 scanned by the probe 50, the repetition of the sending steps 110, of the receiving steps 120, of the analyzing steps 130 and of the determination steps 140. Thus, for each region to be checked of the external sheath 30, the medium M in the annular space 33 between the internal surface 32 of the external sheath 30 and the second layer of armors 25 facing the region to be checked of the external sheath 30, is determined.

Thus, the checking method gives the possibility of determining the flooding level of the annular space 33 of a flexible conduit 2 all along the conduit 2 and whatever the external pressure applied to the conduit 2.

In particular, in the case when the coupling pressure between the external sheath 30 and the layers of external armors 24, 25 exceeds a few tens of bars, the method gives the possibility of reliably distinguishing a dry annular space from a flooded annular space.

The checking method is further non-intrusive and simple to apply.

Alternatively, the flexible conduit 2 includes an intermediate layer between the external sheath 30 and the second layer of armors 25. The intermediate layer is for example a layer of scotch® tape or adhesive. In this case, the analyzed reflected signal is the signal at the interface between the internal surface 32 of the region to be checked and the annular space 33 in which the intermediate layer is found.

As the checking method is not intrusive, it is able to be applied during the use of the flexible line, without interrupting its use, for example during transport of fluid through the central passage 16.

The invention claimed is:

1. A method for checking a flexible line, the flexible line comprising at least one layer of armors surrounded with an external sheath, the external sheath delimiting an internal space receiving the layer of armors and comprising at least one medium at an interface between the external sheath and the internal space, the method comprising:
   sending an incident ultrasonic signal from an outside of the external sheath on a region to be checked of the external sheath,
   receiving a reflected signal at the interface between the region to be checked of the external sheath and the internal space facing the region to be checked of the external sheath, and
   analyzing polarity of the reflected signal at the interface,
   determining amplitude of the reflected signal at the interface and calculating a ratio of amplitudes between the reflected signal and the incident signal, and
   determining, depending on the analyzed polarity and on the calculated ratio of amplitudes, at least the nature of the at least one medium at the interface.

2. The checking method according to claim 1, wherein during the analyzing step, not rectifying the reflected signal.

3. The checking method according to claim 1, wherein the method further includes, scanning of a plurality of regions to be successively checked of the external sheath and for each region to be checked of the external sheath, repeating the sending, receiving and analyzing steps for determining the medium at the interface between the region to be checked of the external sheath and the internal space facing the region to be checked of the external sheath.

4. The checking method according to claim 3, wherein the scanning is at a pitch comprised between 0 millimeter and 10 millimeters.

5. The checking method according to claim 3, wherein the scanning is carried out at least one of axially along the flexible line and angularly around the flexible line.

6. The checking method according to claim 1, wherein the sent ultrasonic signal has a central frequency selected between 1.5 MHz and 5 MHz.

7. The checking method according to claim 1, further comprising sending the ultrasonic signal as a focused ultrasonic beam.

8. The checking method according to claim 1, further comprising sending and receiving the ultrasonic signal by a piezo-electric sensor.

9. The checking method according to claim 1, wherein, during the determining, comparing the reflected signal with a database of ultrasonic signals.

10. The checking method according to claim 1, wherein the flexible line includes an intermediate layer between the external sheath and the layer of armors.

11. The checking method according to claim 1, wherein the medium is a liquid, a gas or a solid.

12. The checking method according to claim 1, wherein the flexible line is a flexible conduit comprising a pressure sheath, the external sheath and the pressure sheath delimiting an annular space forming the internal space receiving the layer of armors.

13. The checking method according to claim 12, wherein when the determined medium is water, the annular space is considered to be flooded at the region to be checked of the external sheath.

14. The method according to claim 13, further comprising determining a flooding level of the annular space.

15. The checking method according to claim 1, further comprising immersing the flexible line in an extend of water.

16. An installation for checking a flexible line, the flexible line comprising at least one layer of armors surrounded with an external sheath, the external sheath delimiting an internal space receiving the layer of armors
   and comprising at least one medium at an interface between the external sheath and the internal space, the installation comprising:
   a probe capable of sending an incident ultrasonic signal onto a region to be checked of the external sheath and of receiving a reflected signal at the interface between the region to be checked of the external sheath and the internal space facing the region to be checked of the external sheath, and
   a data processing unit configured for analyzing polarity of the reflected signal at the interface, for determining amplitude of the reflected signal at the interface, for calculating a ratio of amplitudes between the reflected signal and the incident signal, and for determining, depending on the analyzed polarity, and on the calculated ratio of amplitudes, at least the nature of the at least one medium at the interface.

17. The checking method according to claim 3, wherein the scanning is at a pitch comprised between 0 millimeter and 2 millimeters.

18. The checking method according to claim 1, wherein the sent ultrasonic signal has a central frequency selected between 2MHz and 2.5 MHz.

* * * * *